United States Patent [19]

Kawamatsu et al.

[11] 4,074,057
[45] Feb. 14, 1978

[54] 2-HALOPROPIONIC ACID AND ITS DERIVATIVES

[75] Inventors: Yutaka Kawamatsu, Kyoto; Takahiro Saraie, Osaka; Eiko Imamiya, Tondabayashi; Yukihiko Hamuro, Hyogo, all of Japan

[73] Assignee: Takeda Chemical Co., Ltd., Japan

[21] Appl. No.: 728,193

[22] Filed: Sept. 30, 1976

Related U.S. Application Data

[63] Continuation-in-part of Ser. No. 531,747, Dec. 11, 1974, abandoned.

[30] Foreign Application Priority Data

Dec. 12, 1973 Japan .................. 48-139199
Apr. 19, 1974 Japan .................. 49-44634
May 22, 1974 Japan .................. 49-58116
Oct. 9, 1974 Japan .................. 49-116559

[51] Int. Cl.$^2$ ............................................. C07C 69/76
[52] U.S. Cl. ............................. 560/55; 260/465 F; 260/501.17; 260/516; 260/520 C; 260/559 D; 260/562 P; 260/571; 260/612 R; 260/599; 560/9
[58] Field of Search .......... 260/473 G, 520 C, 559 D

[56] References Cited

U.S. PATENT DOCUMENTS

| 2,128,975 | 9/1938 | Van Duzee et al. ............ 260/473 R |
| 3,649,679 | 3/1972 | Marshall .......................... 260/473 R |
| 3,983,164 | 9/1976 | Thorne ............................. 260/473 R |

FOREIGN PATENT DOCUMENTS

| 2,150,778 | 1973 | France .............................. 260/473 G |

*Primary Examiner*—Paul J. Killos
*Attorney, Agent, or Firm*—Wenderoth, Lind & Ponack

[57] ABSTRACT

Compounds of the formula:

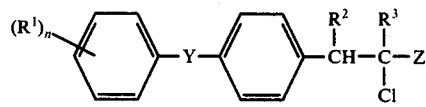

wherein $R^1$ represents hydrogen, lower alkyl having 1 to 5 carbon atoms, halogen, hydroxyl, lower alkoxy having 1 to 4 carbon atoms or trifluoromethyl; $R^2$ and $R^3$ are the same or different and each represents hydrogen or a lower alkyl having 1 to 5 carbon atoms; Y represents an alkylenethio group having 1 to 6 carbon atoms, alkyleneoxy having 1 to 6 carbon atoms, or alkylenedioxy having 1 to 6 carbon atoms; Z represents a carboxyl group or a group convertible to carboxyl and n is 1 or 2. The compounds have utility in treatment of hyperlipemia and diabetes.

30 Claims, No Drawings

2-HALOPROPIONIC ACID AND ITS DERIVATIVES

This is a continuation-in-part of Ser. No. 531,747 filed Dec. 11, 1974, now abandoned.

The present invention relates to a novel compound of the following general formula (I):

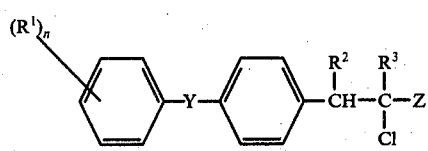

wherein $R^1$ represents hydrogen atom, lower alkyl having 1 to 5 carbon atoms, halogen, hydroxyl, lower alkoxy having 1 to 4 carbon atoms or trifluoromethyl; $R^2$ and $R^3$ are the same or difference and each represents hydrogen or a lower alkyl having 1 to 5 carbon atoms; Y represent an alkylenethio group having 1 to 6 carbon atoms, an alkyleneoxy group having 1 to 6 carbon atoms or an alkylenedioxy group having 1 to 6 carbon atoms; Z represents carboxyl or a group convertible to a carboxyl; $n$ is 1 or 2.

The present inventors have made extensive studies on a series of 2-halopropionic acid and its derivatives and succeeded in synthesizing the novel compound of the above formula (I), and have found that the above compounds have remarkable hypolipidemic, hypoglycemic and other biological activities.

French Pat. No. 2,150,778 discloses in Example 14 the compound α-bromo-β-(p-benzyloxy)phenylpropionic acid as a chemical intermediate. However, no other utility is disclosed. Moreover, this compound has been tested and has been found inferior with the corresponding 2-chloro compound of the present invention in hypolipidemic activity. Similar results have been obtained for other bromo analogs of the present 2-chloro compounds.

Netherlands application No. 7,117,006 discloses various α-halophenoxyphenylacetic acid derivatives with anti-inflammatory activity and these are structurally remote from the present compounds.

The principal object of this invention is to provide novel chloro compounds of the formula (I) useful as medicines such as remedies for hyperlipemia.

Another object of this invention is to provide methods for the production of these novel compounds.

Further objects will be made apparent from the description and claims hereinafter given.

The lower alkyl group having 1 to 5 carbon atoms represented by $R^1$, $R^2$ and $R^3$ may be straight or branched and is exemplified by methyl, ethyl, n-propyl, isopropyl, n-butyl, isobutyl, sec-butyl, tert-butyl, n-pentyl, isopentyl, neopentyl or the like. The halogen atom represented by $R^1$ is enumerated by chlorine, bromine, iodine and fluorine. The alkoxy group having 1 to 4 carbon atoms represented by $R^1$ is exemplified by methoxy, ethoxy, n-propoxy, isopropoxy, n-butoxy, isobutoxy, tert-butoxy. The alkyleneoxy group having 1 to 6 carbon atoms represented by Y may be straight or branched and is exemplified by

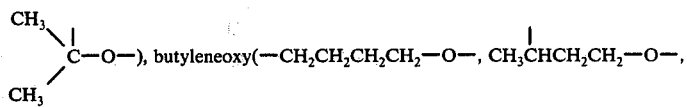

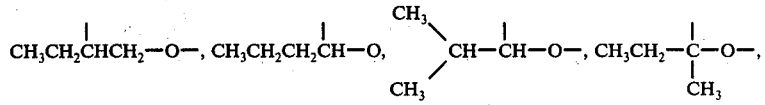

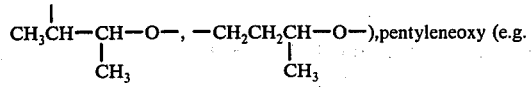

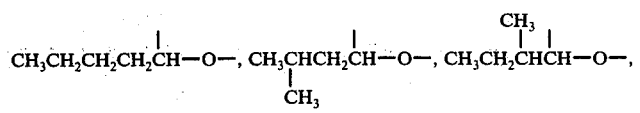

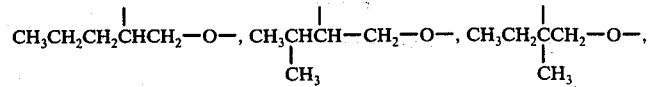

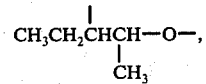

-continued $$CH_3CH_2CH_2\overset{\overset{CH_2-}{|}}{CH}-O-, \quad CH_3CH_2\overset{|}{C}HCH_2CH_2-O-, \quad CH_3\overset{|}{C}HCH_2CH_2-O-,$$
$$\overset{}{\phantom{X}} \qquad\qquad\qquad\qquad\qquad\qquad\qquad\qquad\qquad CH_3$$

$$CH_3\overset{|}{C}H\overset{}{C}HCH_2-O-, \quad -CH_2\overset{|}{C}HCH_2-O-, \quad CH_3\overset{|}{C}HCH_2CH_2CH_2-O-,$$
$$\phantom{X}CH_3 \qquad\qquad CH_3CH_2$$

$$-CH_2\overset{|}{C}HCH_2CH_2-O-, \quad -CH_2CH_2\overset{|}{C}HCH_2-O-, \quad -CH_2CH_2CH_2CH_2CH_2-O-)$$
$$\phantom{X}CH_3 \qquad\qquad\qquad\qquad CH_3$$

and hexyleneoxy (e.g. $CH_3CH_2CH_2CH_2CH_2\overset{|}{C}H-O-, \quad CH_3\overset{|}{C}HCH_2CH_2\overset{|}{C}H-O-,$
$$\phantom{XXXXXXXXXXXXXXXXXXXXXXXXXXXXXXXXXXXXXXXXXXXXXXXXXXXX} CH_3$$

$$\overset{CH_3}{\underset{CH_3}{CH_3\overset{|}{C}}} CH_2CH-O-, \quad CH_3CH_2CH_2CH_2\overset{|}{C}HCH_2-O-, \quad CH_3\overset{|}{C}HCH_2\overset{|}{C}H-CH_2-O-,$$
$$\phantom{XXXXXXXXXXXXXXXXXXXXXXXXXXXXXXXXXXXXXXXXXX} CH_3$$

$$\overset{CH_3}{\underset{CH_3}{CH_3\overset{|}{C}-}}\overset{|}{C}H-CH_2-O-, \quad CH_3CH_2CH_2\overset{|}{C}HCH_2CH_2-O-, \quad CH_3\overset{|}{C}H\overset{|}{C}H-CH_2CH_2-O-,$$
$$\phantom{XXXXXXXXXXXXXXXXXXXXXXXXXXXXXXXXXXXXXXXXXX} CH_3$$

$$CH_3CH_2\overset{|}{C}HCH_2CH_2CH_2-O-, \quad CH_3\overset{|}{C}HCH_2CH_2CH_2O-, \text{ )}.$$

The alkylenedioxy group having 1 to 6 carbon atoms represented by Y may be straight or branched and is exemplified by methylenedioxy ($-O-CH_2-O-$), ethylenedioxy ($-O-CH_2CH_2-O-, \quad -O-\overset{|}{C}H-O-$),
$$\phantom{XXXXXXXXXXXXXXX} CH_3$$

propylenedioxy($-O-CH_2CH_2CH_2O-, \quad -O-\overset{|}{C}HCH_2-O-, \quad -O-\overset{|}{C}H-O-$),
$$\phantom{XXXXXXXXXXXXXXXXXXXXXXXXXXXXX} CH_3 \qquad\qquad CH_2$$
$$\phantom{XXXXXXXXXXXXXXXXXXXXXXXXXXXXXXXXXXXXXXXXXXXXXXXX} CH_3$$

butylenedioxy(e.g. $-O-CH_2CH_2CH_2CH_2-O-, \quad -O-CH_2\overset{|}{C}HCH_2-O-,$
$$\phantom{XXXXXXXXXXXXXXXXXXXXXXXXXXXXXXXXXXXXXXXXXXXXXX} CH_3$$

$-O-\overset{|}{C}H \overset{|}{C}H-O-$) pentylenedioxy (e.g. $-O-CH_2CH_2CH_2CH_2-O-,$
$$\phantom{X}CH_3 CH_3$$

$$-O-\overset{|}{C}HCH_2CH_2CH_2-O-, \quad -O-CH_2\overset{|}{C}HCH_2CH_2-O-, \quad -O-\overset{|}{C}H-\overset{|}{C}HCH_2-O-,$$
$$\phantom{X}CH_3 \qquad\qquad\qquad\qquad CH_3 \qquad\qquad\qquad\qquad CH_3 \; CH_3$$

$$-O-\overset{|}{C}HCH_2\overset{|}{C}H-O-, \quad -O-\overset{|}{C}H \; CH_2CH_2-O-), \text{ hexylenedioxy (e.g.}$$
$$\phantom{X}CH_3 \quad CH_3 \qquad\qquad CH_2CH_3$$

$$-O-CH_2CH_2CH_2CH_2CH_2CH_2-O-, \quad -O-\overset{|}{C}HCH_2CH_2CH_2CH_2-O-,$$
$$\phantom{XXXXXXXXXXXXXXXXXXXXXXXXXXXXXXXXXXXXXX} CH_3$$

$$-O-CH_2\overset{|}{C}HCH_2CH_2CH_2-O-, \quad -O-CH_2CH_2\overset{|}{C}HCH_2CH_2-O-,$$
$$\phantom{X}CH_3 \qquad\qquad\qquad\qquad\qquad\qquad CH_3$$

$$-O-\overset{|}{C}HCH_2CH_2CH_2-O-, \quad -O-CH_2\overset{|}{C}HCH_2CH_2-O-, \quad -O-\overset{|}{C}H\overset{|}{C}HCH_2CH_2-O-,$$
$$\phantom{X}CH_2CH_3 \qquad\qquad\qquad\qquad CH_2CH_3 \qquad\qquad\qquad CH_3$$
$$\phantom{XXXXXXXXXXXXXXXXXXXXXXXXXXXXXXXXXXXXXXXXXXXXXXXXXXXXX} \overset{CH_3}{\phantom{X}}$$

$$-O-CH_2\overset{|}{C}H\overset{|}{C}HCH_2-O- \quad -O-CH_2\overset{|}{C}H-CH_2-O-).$$
$$\phantom{X}CH_3 \qquad\qquad\qquad\qquad CH_2CH_2CH_3$$

The alkylenethio group having 1 to 6 carbon atoms represented by Y may be straight or branched and is exemplified by methylenethio ($-CH_2-S-$), ethylenethio ($-CH_2-CH_2-S-, \quad -\overset{|}{C}H-S-$), propylenethio ($-CH_2CH_2CH_2-S-, \quad CH_3\overset{|}{C}HCH_2-S-,$
$$\phantom{XXXXXXXXXXXXXXXXX} CH_3$$

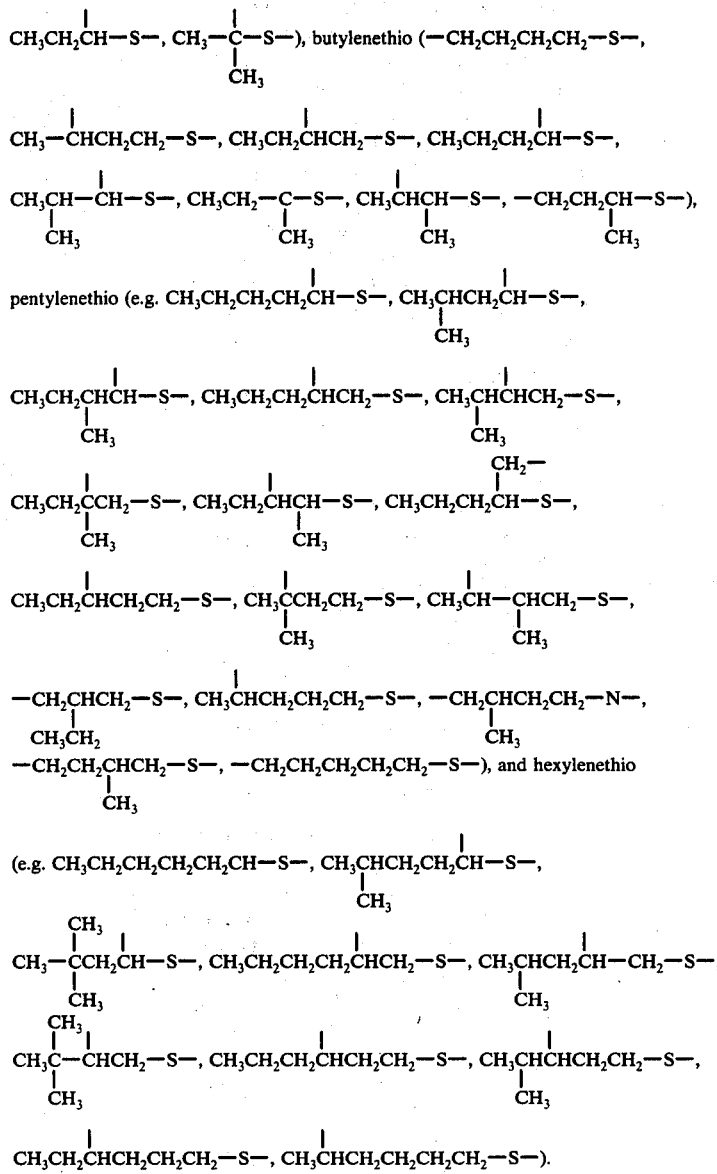

As the group convertible to carboxyl group, represented by Z, there are exemplified by formyl group, cyano group, aminocarbonyl group, an alkoxycarbonyl group having 2 to 5 carbon atoms (e.g. methoxycarbonyl, ethoxycarbonyl, n-propoxycarbonyl, i-propoxycarbonyl, n-butoxycarbonyl, isobutoxycarbonyl, tert-butoxycarbonyl, sec-butoxycarbonyl), a mono- or di-alkylaminocarbonyl group having 2 to 9 carbon atoms (e.g. N-methylaminocarbonyl, N,N-dimethylaminocarbonyl, N-ethylaminocarbonyl, N,N-diethylaminocarbonyl, N-n-propylaminocarbonyl, N,N-di-n-propylaminocarbonyl, N-isopropylaminocarbonyl, N,N-diisopropylaminocarbonyl, N-n-butylaminocarbonyl, N,N-di-n-butylaminocarbonyl), mono- or dicycloalkylaminocarbonyl having 6 to 13 carbon atoms (e.g. N-cyclopentylaminocarbonyl, N,N-dicyclopentylaminocarbonyl, N-cyclohexylaminocarbonyl, N,N-dicyclohexylaminocarbonyl), mono- or diarylaminocarbonyl having 7 to 16 carbon atoms (e.g. N-phenylaminocarbonyl, N,N-diphenylaminocarbonyl, N-tolylaminocarbonyl, N,N-ditolylaminocarbonyl). The compound (I) wherein Z is carboxyl group includes pharmaceutically acceptable salts thereof. As the pharmaceutically acceptable salts, there are exemplified by a salt of carboxylic acid with nontoxic cations (e.g. sodium, potassium, lithium, calcium, magnesium, ammonium etc.) or with organic amines such as polyhydroxyalkylamines (e.g. N-methylglucamine, diethanolamine, triethanolamine, trishydroxymethylaminomethane).

The compounds of general formula (I) have prominent hypolipidemic and hypoglycemic activity and show low toxicity and side effect. Taking advantage of these properties these compounds can safely be used as remedies for hyperlipemia and diabetes in mammals including human beings. When a compound (I) is used as such as medicine, it can be administered, either as it is or in admixture with a pharmaceutically acceptable vehicle, excipient or/and diluent, orally or parenterally in various dosage forms such as powders, granules, tablets, capsules, suppositories and injections. When any of the compounds is used for the purpose of treating hyperlipemia, it may be administered orally or non-orally in amounts of 0.03 - 1.0 g. per day for a human adult. When any of the compounds is used for the purpose of treating diabetes, it may be administered orally or non-orally in amounts of 0.1 - 3.0 g. per day for a human adult.

The compounds of formula (I) can be prepared by reacting a diazonium salt of formula (II):

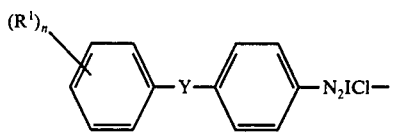

wherein $R^1$, Y and $n$ have the same meanings as given above, with an ethylene compound of the general formula (III): acetonitrile,

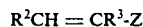

wherein $R^2$, $R^3$ and Z have the same meanings as given above.

This reaction is conducted with advantage in a slight molecular excess of ethylene compound (III) relative to diazonium salt (II). The reaction is commonly carried out in a solvent. As the solvent, there are exemplified water, methanol, ethanol, n-propanol, acetone, methyl ethyl ketone, diethyl ketone, ethyl propyl ketone, acetonitrile, N-methylpyrrolidone, dimethylsulfoxide, sulfolane, etc. as well as mixtures of such solvents. This reaction is conducted with more advantage by adding hydrochloric acid to the reaction system. When a solvent containing hydrochloric acid is used, diazonium salts (II) other than the chloride can be employed as a starting material in this invention. Moreover, this reaction may be accelerated with advantage by using a catalyst. As the catalyst, copper compounds, for instance, may be employed. Thus, cuprous oxide, cupric oxide, cuprous chloride, cupric chloride, cuprous bromide, cupric bromide, copper nitrate, copper sulfate, etc. are more commonly employed. Among them, use of cuprous oxide is the most preferable. The proportion of the catalyst is ordinarily 0.02 to 0.2, preferably 0.05 to 0.1, mole per mole of diazonium salt (II). To control the reaction velocity, the above-mentioned catalyst may be used in an increased amount or in a reduced amount. The temperature, time, pressure and other conditions of the reaction are selected according to the particular starting materials, solvent and catalyst and so on. Ordinarily the reaction proceeds smoothly at a temperature under cooling with ice to room temperature.

When Z in compound thus obtained is a carboxyl group, it may be converted by a per se known manner to a pharmaceutically acceptable salt of carboxyl group with a nontoxic cation or with a organic amine which are mentioned hereinbefore or to an ester such as methyl ester, ethyl ester, n-propyl ester, isopropyl ester. When Z in compound (I) is a group convertible to carboxyl group, the group may be converted to a carboxyl group in a per se known manner. When Z is a cyano group, an alkoxycarbonyl group or an aminocarbonyl group which is substituted or unsubstituted, it can be converted to a carboxyl group by means of hydrolysis, whereas when Z is formyl group, it can be oxidized to a carboxyl group. When Z is cyano group, it can also be converted to amino carbonyl group. For instance, the hydrolysis may be effected by treating the compound (I) with such an acid as hydrochloric acid, sulfuric acid, nitric acid, phosphoric acid or carbonic acid or with such a base as sodium hydroxide, potassium hydroxide, sodium carbonate or potassium carbonate. In this reaction, such an alcohol as methanol or ethanol may be allowed to be present as required. The oxidation of the formyl group can be accomplished by permitting an oxidation agent to act upon the compound (I) in a suitable solvent. Examples of said oxidizing agent include potassium dichromate, potassium chromate, potassium permanganate, hydrogen peroxide, barium peroxide, peracetic acid, perbenzoic acid, hypochlorous acid and ozone. The temperature, time and other conditions of the above-mentioned hydrolysis and oxidation reaction are selected according to such factors as the desired compound (I), solvent and procedure followed.

The compound (I) thus obtained may be separated and purified by per se known separation-purification procedure such as crystallization, recrystallization, concentration, distillation, chromatography, etc.

The starting material diazonium salt (II) can be prepared by diazotizing the corresponding amino compound in the presence of hydrochloric acid in a conventional manner or by oringing a diazonium salt (II) wherein Cl is an anion other than halogen into contact with hydrochloric acid.

Throughout the present specification, the abbreviations "mg.", "g.", "ml.", "m.p.", "b.p." and "° C", respectively refer to "milligram(s)", "gram(s)", "milliliter(s)", "melting point", "boiling point" and "degree(s) centigrade".

REFERENCE EXAMPLE 1

In 120 ml. of ethanol is dissolved 31.2 g. of phenol to which are added 24 g. of a methanol solution containing 28% of sodium methoxide and 0.3 g. of potassium iodide. Then 20 g. of 4-(2-bromoethyl)acetanilide is added to the mixture, and the mixture is refluxed for 3.5 hours. After the solvent is distilled off, an aqueous solution of sodium hydroxide in 200 ml. of water is added to the residue, and cyrstals formed are collected by filtration. Recrystallization from ethyl acetate gives 12 g. of 4-(2-phenoxyethyl)acetanilide, melting at 121°-123° C.

To a mixed solution of 30 ml. of hydrochloric acid and 20 ml. of water is added 10 g. of 4-(2-phenoxyethyl)acetanilide and the mixture is refluxed for 2 hours. After cooling, crystals formed are collected by filtration. Recrystallization from water gives 7.5 g. of 4-(2-phenoxyethyl) aniline hydrochloride, melting at 189°-191° C.

REFERENCE EXAMPLE 2

A mixture of 37.8 g. of 1-phenyl-1-bromo-2-methylpropane, 23.6 g. of p-nitrophenol, 150 ml. of ethanol and 9.5 g of sodium methoxide is refluxed for 5 hours. After the reaction has been completed, ethanol is distilled off and the residue is subjected to extraction with ether. The extract is washed with 5% aqueous solution of sodium hydroxide and then with water. After drying with magnesium sulfate, the solvent is distilled off. Thus-obtained red oily substance of crude 1-phenyl-1-(4-nitrophenoxy)-2-methylpropane is dissolved in 100 ml. of methanol, and subjected to catalytic reduction using palladium-carbon. After the reduction has been completed, the catalyst is removed by filtration. The oily substance obtained by removing the solvent is dissolved in 50 ml. of ether, and concentrated hydrochloric acid is added to the solution to give 4-(1-phenyl-2- methylpropyloxy) aniline hydrochloride, melting at 165°-168° C.

REFERENCE EXAMPLE 3

A mixture of 240 g of p-chlorobenzyl chloride, 240 g. of p-acetaminophenol, 850 ml. of ethanol and 290 g. of a 28% methanolic solution of sodium methoxide is stirred under heating over a mantle heater. The reaction begins abruptly in the neighborhood of 65° C and the mixture starts undergoing a vigorous reflux. (The mantle heater is removed.) The reaction mixture is refluxed for 2.5 hours, after which about 700 ml. of the solvent is distilled off. The residue is poured in one liter of a 4% aqueous solution of NaOH (containing ice) and the resultant precipitate 4-acetaminophenoxy-4-chlorophenylmethane (white crystals) is collected by filtration.

The white crystals obtained in above procudure are not dried but are directly dissolved in 1.5 kg. of n-propanol and, after the addition of 120 g. of NaOH granules, the solution is refluxed under stirring for 5 hours. After the reaction has been completed, the mixture is concentrated under reduced pressure to remove about 600 ml. of the solvent and, under stirring, 2 kg. of ice-water is added. The resultant precipitate 4-(4-chlorobenzyloxy)aniline (brown granules) is collected by filtration and washed with water. Yield 324 g. Melting point: 102° C.

REFERENCE EXAMPLE 4

In 500 ml. of methanol is dissolved 25 g. of 4-(4-chlorophenoxymethyl)nitrobenzene and, with the addition of Raney nickel, the solution was shaken in hydrogen streams. A total of 2.5 ml. of hydrogen is absorbed. The Raney nickel is filtered off and the filtrate is concentrated to about 40 ml. The resultant crystals are collected by filtration. The procedure yields 3.5 g. of 4-(4-chlorophenoxymethyl)aniline, melting at 125°-126° C.

EXAMPLE 1-(1)

In 500 ml. of acetone is dissolved 94 g. of 4-(4-chlorobenzyloxy)aniline and, at room temperature, a mixture of 200 g. of hydrochloric acid and 100 g. of water is added. The solution is cooled well with ice. While the solution is stirred, a solution of 30.8 g. of sodium nitrite in 100 ml. of water, then 100 g. of ethyl acrylate and, finally, 5.8 g. of powdery cuprous oxide are added. Nitrogen gas is evolved in small increments. The ice bath is removed after 10 minutes and, at 12° C, 5.8 g. of cuprous oxide is further added. With the evolution of nitrogen gas at a moderate rate, the temperature increases gradually. The mixture is stirred at room temperature for 7 hours. After the reaction has been completed, the reaction mixture is concentrated under reduced pressure and extracted with ethyl acetate. The ethyl acetate is distilled off and the residual red-colored oil is purified by chromatography on silica gel. The described procedure yields 70 g. of ethyl 2-chloro-3-(4-(4-chlorobenzyloxy)phenyl)propionate as a yellowish oily product. Cyclohexane/benzene is used as the eluant solvent (First 1:1 and then 1:4).

NMR spectrum($\delta$ ppm, CCl$_4$):

1.17(3H, t), 3.01 - 3.21(2H, m), 4.08(2H, q), 4.23 (1H, t), 4.89(2H, s), 6.74(2H, d), 7.02(2H, d), 7.22(4H, s)

EXAMPLES 1-(2) – 1-(37)

By a similar manner to Example 1-(1), the following compounds are produced.

| Example | Produced-compound | Starting compounds |
|---|---|---|
| 1-(2) | 2-chloro-3-(4-(4-chlorobenzyloxy)phenyl)-propionic acid m.p.119–121° C | 4-(4-chlorobenzyloxy)-aniline,acrylic acid |
| 1-(3) | ethyl 2-chloro-5-(4-(2-chlorobenzyloxy)-phenyl)propionate yellow oily substance NMR spectrum ($\delta$ppm,CDCl$_3$) 1.16(3H,t),3.07–3.26 (2H,m),4.13(2H,q),1.38 (1H,t),5.07(2H,s),6.79–7.60(8H,m) | 1-(2-chlorobenzyloxy) aniline,ethyl acrylate |
| 1-(4) | ethyl 2-chloro-3-(1-(4-methylbenzyloxy)phenyl)-propionate m.p.20–24° C NMR spectrum($\delta$ppm.CDCl$_3$) 1.22(3H,t),2.37(2H,s), 3.23(2H,m),4.20(2H,q), 4.40(1H,t),5.02(2H,s), 6.74–7.54(8H,m) | 4-(4-methyl-benzyloxy)-aniline,ethyl acrylate |
| 1-(5) | ethyl 2-chloro-3-(1-(4-methoxybenzyloxy)-phenyl)propionate NMR spectrum($\delta$ppm,CDCl$_3$) 1.13(3H,t),3.15(2H,m), 3.68(3H,s),4.10(2H,q), 4.35(1H,t),4.86(2H,s), 6.7–7.5(8H,m) | 4-(4-methoxy-benzyloxy)-aniline,ethyl acrylate |
| 1-(6) | ethyl 2-chloro-3-(4-benzyloxyphenyl)-propionate yellow oily substance NMR spectrum($\delta$ppm,CDCl$_4$) 1.12(3H,t),3.00–3.22 (2H,m),4.06(2H,q), 4.25(1H,t),4.90(2H,s), 6.80(2H,d),7.01(2H,d), 7.27(5H,s) | 4-benzyloxy-aniline,ethyl acrylate |
| 1-(7) | methyl 2-chloro-2-methyl-3-(4-(2-fluorobenzyloxy)-phenyl)propionate yellow oil NMR spectrum ($\delta$ppm,CDCl$_3$) 1.6(3H,s),3.3(2H,s), 3.7(3H,s),5.1(2H,s), 7.2(8H,m) | 4-(2-fluoro-benzyloxy)-aniline,methyl methacrylate |
| 1-(8) | ethyl 2-chloro-3-(4-(2-phenylethyloxy)phenyl)-propionate yellow oily substance NMR spectrum($\delta$ppm,CDCl$_3$) 1.2(3H,t),3.2(4H,m), 4.2(5H,m),6.8(2H,d), 7.1(2H,d),7.25(5H,s) | 4-(2-phenyl-ethyloxy) aniline,ethyl acrylate |
| 1-(9) | methyl 2-chloro-3-(4-(2-phenylethyloxy)phenyl)-propionate red oily substance IR spectrum(cm$^{-1}$, 1740,1605,1505,1240, 1015,750,700 | 4-(2-phenyl-ethyloxy)-aniline,methyl acrylate |
| 1-(10) | ethyl 2-chloro-3-{4-(2-(4-chlorophenoxy)-ethyloxy]phenyl-propionate needles m.p.81–82° C | 4-(2-(4-chloro-phenoxy)ethyloxy]-aniline,ethyl acrylate |
| 1-(11) | ethyl 2-chloro-3-(4-(4-chlorophenoxymethyl)-phenyl)propionate NMR spectrum($\delta$ppm,CDCl$_3$) 1.20(3H,t),3.22(2H,m), 4.07(2H,q),4.43(1H,t), 4.97(2H,s),6.7–7.5 (8H,m) | 4-(4-chloro-phenoxymethyl)-aniline,ethyl acrylate |
| 1-(12) | 2-chloro-3-(4-benzyloxy-phenyl)propionamide m.p.134–135° C | 4-benzyloxy-aniline acrylamide |
| 1-(13) | 2-chloro-3-(4-(2-phenylethyloxy)phenyl)-propionamide m.p.101° C | 4-(2-phenyl-ethyloxy)-aniline acrylamide |
| | ethyl 2-chloro-3-(4-(3-phenylpropyloxy)phenyl)-propionate | 4-(3-phenyl- |

-continued

| Example | Produced-compound | Starting compounds |
|---|---|---|
| 1-(14) | oily substance NMR spectrum(δppm,CDCl₃) 1.20(3H,t),2.09(2H,m), 2.80(2H,t),3.20(2H,t), 3.93(2H,t),4.18(2H,q), 4.39(1H,t),6.80(2H,d), 7.10(2H,d),7.20(5H,s) | propyloxy)-aniline ethyl acrylate |
| 1-(15) | ethyl 2-chloro-3-(4-(4-phenylbutyloxy)phenyl]-propionate yellow oily substance NMR spectrum(δppm,CDCl₃) 1.17(3H,t),1.73(4H,m), 2.63(2H,t),3.15(2H,m), 3.87(2H,t),4.10(2H,q), 4.33(1H,t),6.7–7.4 (9H,m) | 4-(4-phenyl-buthyloxy-aniline,ethyl acrylate |
| 1-(16) | ethyl 2-chloro-3-(4-benzylthiophenyl)-propionate oily substance NMR spectrum(δppm,CDCl₃) 1.20(3H,t),3.20(2H,m), 4.09(2H,s),4.18(2H,q), 4.40(1H,t),6.90–7.60 (9H,m) | 4-benzylthio-aniline hydro-chloride ethyl acrylate |
| 1-(17) | ethyl 2-chloro-3-(4-(4-fluorobenzyloxy)phenyl)-propionate NMR spectrum(δppm,CDCl₃) 1.09(3H,t),3.15(2H,m), 4.06(2H,q),4.35(1H,t), 4.83(2H,s),6.7–7.5 (8H,m) | 4-(4-fluoro-benzyloxy)-aniline,ethyl acrylate |
| 1-(18) | ethyl 2-chloro-3-(4-(3-fluorobenzyloxy)phenyl)-propionate oily substance NMR spectrum(δppm,CDCl₃) 1.17(3H,t),3.19(2H,m), 4.13(2H,q),4.36(1H,t), 4.97(2H,s),6.67–7.53 (8H,m) | 4-(3-fluoro-benzyloxy)-aniline hydrochloride ethyl acrylate |
| 1-(19) | ethyl 2-chloro-3-(4-(2-fluorobenzyloxy)phenyl)-propionate yellow oily substance NMR spectrum(δppm,CDCl₃) 1.19(3H,t),2.87–3.53 (2H,m),4.16(2H,q), 4.39(1H,t),5.08(2H,s), 6.82–7.62(8H,m) | 4-(2-fluoro-benzyloxy)-aniline,ethyl acrylate |
| 1-(20) | 2-chloro-3-(4-(3-chloro-benzyloxy)phenyl)pro-pionic acid m.p.88–89° C | 4-(3-chloro-benzyloxy)-aniline acrylic acid |
| 1-(21) | ethyl 2-chloro-3-[4-(3-trifluoromethylbenzyloxy)-phenyl]propionate oily substance NMR spectrum(δppm,CDCl₃) 1.20(3H,t),3.20(2H,m), 3.80–4.60(3H,m),5.05 (2H,s),6.70–7.90(8H,m) | 4-(3-trifluoro-methylbenzyloxy)-aniline,ethyl acrylate |
| 1-(22) | N-phenyl-2-chloro-3-(4-(4-chlorobenzyloxy)-phenyl)propionamide white crystal m.p.177–178° C | 4-(4-chloro-benzyloxy)-aniline, N-phenyl-acrylamide |
| 1-(23) | N-isopropyl-2-chloro-3-(4-(2-phenylethyloxy)-phenyl)propionamide white crystal m.p.98–99° C | 4-(2-phenyl-ethyloxy)-aniline, N-isopropyl-acrylamide |
| 1-(24) | N-methyl-N-(n-butyl)-2-chloro-3-(4-(2-phenyl-ethyloxy)phenyl)-propionamide oily substance NMR spectrum(δppm,CDCl₄) 0.91(3H,t),1.33(4H,or), 2.84(3H,d),3.09(2H,t), 3.27(2H,t),2.80–3.63(2H, m),4.08(2H,t),4.33–4.56 (1H,m),6.73(2H,d),7.07 (2H,d),7.16(5H,c) | 4-(2-phenyl-ethyloxy)-aniline N-methyl-N-(n-butyl)-acrylamide |
| 1-(25) | ethyl 2-chloro-3-(4-phenoxymethylphenyl)-propionate NMR spectrum(δppm,CDCl₃) 1.17(3H,t),3.21(2H,m), | 4-phenoxy-methylaniline ethyl |
| 5 | 4.11(2H,q),4.40(1H,t), 4.97(2H,s),6.7–7.5 (5H,m) ethyl 2-chloro-3-(4-(1-phenylethyloxy)phenyl)-propionate yellow oily substance | acrylate |
| 1-(26) | NMR spectrum(δppm,CDCl₃) 1.10(3H,t),1.58(3H,d), 2.79–3.43(2H,m),4.07 (2H,q),4.30(1H,t), 5.23(1H,q),6.77(2H,d), 6.96(2H,d),7.23(5H,s) | 4-(1-phenyl-ethyloxy)-aniline ethyl acrylate |
| 1-(27) | ethyl 2-chloro-3-(4-(2-phenoxyethyloxy)phenyl]-propionate m.p.80–81° C | 4-(2-phenoxy-ethyloxy)aniline ethyl acrylate |
| 1-(28) | ethyl 2-chloro-3-(4-(1-phenylpropyloxy)phenyl)-propionate yellow oily substance NMR spectrum(δppm,CDCl₃) 0.93(3H,t),1.09(3H,t), 1.83(2H,m),2.77–3.49 (2H,m),4.07(2H,q), 4.29(1H,t),4.95(1H,t), 6.76(2H,d),6.97(2H,d), 7.23(5H,s) | 4-(1-phenyl-propyloxy)-aniline ethyl acrylate |
| 1-(29) | ethyl 2-chloro-3-(4-(1-phenylbutyloxy)phenyl)-propionate yellow oily substance NMR spectrum(δppm,CDCl₃) 0.77–2.13(7H,m),1.13(3H, t),2.78–3.43(2H,m), 4.08(2H,q),4.33(1H,t), 5.05(1H,t),6.76(2H,d), 6.96(2H,d),7.26(5H,s) | 4-(1-phenyl-butyloxy)-aniline ethyl acrylate |
| 1-(30) | ethyl 2-chloro-3-(4-(1-phenyl-2-methylpropyloxy)-phenyl)propionate yellow oily substance NMR Spectrum(δppm, CDCl₃) 0.85–1.29(9H,m),1.87– 2.43(1H,m), 2.79–3.47 (2H,m), 4.11(2H,q), 4.35 (1H,t),4.77(1H,d),6.76 (2H,d),7.00(2H,d), 7.27(5H,s) | 4-(1-phenyl-2-methyl-propyloxy)-aniline ethyl acrylate |
| 1-(31) | ethyl 2-chloro-3-(4-(1-phenylpentyloxy)phenyl)-propionate oily substance NMR spectrum(δppm, CDCl₃) 0.67–2.30(12H,m),3.10 (2H,m),4.17(2H,m), 4.37(1H,t),5.08(1H,t), 6.90(4H,q),7.30(5H,s) | 4-(1-phenyl-pentyloxy)-aniline ethyl acrylate |
| 1-(32) | ethyl 2-chloro-3-(4-(1-phenoxyethyl)phenyl)-propionate NMR spectrum(δppm,CDCl₃) 1.12(3H,t), 1.56(3H,d), 3.16(2H,m),4.08(2H,q), 4.38(1H,t),5.21(1H,q), 6.67–7.4(9H,m) | 4-(1-phenoxy-ethyl)aniline ethyl acrylate 7.4(9H,m) |
| 1-(33) | ethyl 2-choro-3-(4-(1-methyl-2-phenylethyloxy)-phenyl)propionate oily substance NMR spectrum(δppm,CDCl₃) 1.17(3H,t),1.20(3H,d), 2.90(4H,m),4.13(2H,q), 4.33(1H,t),4.46(1H,m), 6.77(2H,d),7.07(2H,d), 7.17(5H,s) | 4-(1-methyl-2-phenyl-ethyloxy)-aniline ethyl acrylate |
| 1-(34) | 2-chloro-3-(4-(1-phenylethyloxy)phenyl)-propionamide brown oil substance NMR spectrum(δppm,CDCl₃) 1.59(3H,d),2.80–3.50 (2H,m),4.26–4.47(1H,m), 5.26(1H,q),6.43(2H,br), 6.80(2H,d),7.04(2H,d), 7.31(5H,d) | 4-(1-phenyl-ethyloxy)aniline acrylamide |
| 1-(35) | N-phenyl-2-chloro-3-(4-(1-phenylethyloxy)phenyl)-propionamide m.p.90–91° C | 4-(1-phenyl-ethyloxy)-aniline M-phenyl acrylamide |

-continued

| Example | Produced-compound | Starting compounds |
|---|---|---|
| 1-(36) | 2-chloro-3-(4-(1-phenylethyloxy)phenyl)-propionic acid colorless oily substance NMR spectrum($\delta$ppm,CDCl$_1$) 1.57(3H,d),3.10(2H,m) 4.27(1H,t),5.17(1H,Q), 6.70(2H,d),6.97(2H,d), 7.20(5H,s),11.53(1H,s). | 4-(1-phenyl-ethyloxy)-aniline acrylic acid |
| 1-(37) | 2-chloro-3-(4-(1-phenylethyloxy)phenyl)-propionic acid yellow oily substance NMR spectrum($\delta$ppm,CDCl$_3$) 0.97(3H,t),1.90(2H,m), 3.10(2H,m),4.33(1H,t), 4.97(1H,t),6.75(2H,d), 7.03(2H,d),7.23(5H,s), 8.67(1H,s) | 4-(1-phenyl-propyloxy)-aniline acrylic acid |

EXAMPLE 2-(1)

In 40 ml. of methanol is dissolved 5.0 g. of ethyl 2-chloro-3-[4-(4-chlorobenzyloxy)phenyl]propionate, and 6.0 g. of a 20% aqueous solution of sodium hydroxide is added. The mixture is stirred at room temperature for 3 hours and the resultant white crystals are collected by filtration and washed with ether. The procedure yields 3.9 g. of sodium 2-chloro-3-[4-(4-chlorobenzyloxy)phenyl]propionate, monohydrate as white crystals melting at 218°–221° C.

EXAMPLES 2-(2) – 2-(4)

By a similar manner to Example 2-(1), the following salts are produced from the corresponding esters.

| Example | Produced salt |
|---|---|
| 2-(2) | sodium 2-chloro-3-(4-benzyloxyphenyl)-propionated-monohydrate m.p. 214–216° C |
| 2-(3) | sodium 2-chloro-3-[4-(1-phenylethoxy)-phenyl]propionate-monohydrate m.p. 171–174° C |
| 2-(4) | sodium 2-chloro-3[4-(1-phenylpropyloxy)-phenyl]propionate m.p. 183–184° C |

EXAMPLE 3-(1)

In 60 ml. of acetone is dissolved 7.5 g. of 4-(2-phenoxyethyl)aniline hydrochloride, followed by the addition of 7.5 ml. of hydrochloric acid, the mixture is kept at not higher than 10° C. Under stirring, a solution of 2.3 g. sodium nitrite in 4.5 ml. water is added, and the mixture is kept at the same temperature for 30 minutes. To the mixture, 25 ml. of theyl acrylate is added and under stirring, cuprous oxide is added in small portions until evolution of gas has ceased. The mixture is subjected to extraction with ether and the extract is washed three times with water, and then the solvent is distilled off. The residue is dissolved in 70 ml. of ethanol, and under stirring and ice cooling, a solution of 1.2 g. of sodium hydroxide in 4 ml. water is added. After one hour, the resultant crystals are collected by filtration and dried. Recrystallization from ligroine gives 4.5 g. of 2-chloro-3-[4-(2-phenoxyethyl)phenyl]propionic acid. Melting point: 97°–99° C.

EXAMPLE 4-(1)

In 40 ml. of methanol is dissolved 6.6 g. of ethyl 2-chloro-3-[4-(1-phenylethyloxy)phenyl]propionate, and under cooling with ice and stirring, a solution of 0.8 g. sodium hydroxide in 1.2 ml. water is added. The mixture is kept under the same condition for 3 hours, after which the solution is neutralized with acetic acid. Then the solution is concentrated to dryness. The residue is washed well with cyclohexane and dissolved in water. After treating with activated carbon, the solution is acidified with hydrochloric acid. The resultant oily substance is extracted with chloroform and the chloroform is distilled off to give 4 g. of 2-chloro-3-[4-(1-phenylethyloxy)phenyl]propionic acid as a colorless oily substance.

NMR spectrum ($\delta$ ppm, CCl$_4$)
1.57(3H,d), 3.10(2H,M), 4.27(1H,t), 5.17(1H,q), 6.70(2H,d), 6.97(2H,d), 7.20(5H,s), 11.53(1H,s).

EXAMPLE 5-(1)

In 40 ml. of ethanol is dissolved 1.46 g. of 2-chloro-3-[4-(4-chlorobenzyloxy)phenyl]propionic acid, followed by the addition of 0.25 g. of potassium hydroxide. The mixture is stirred at room temperature for 1 hour and the resultant crystals are collected by filtration. These crystals are recrystallized from water to obtain 1.2 g. of potassium 2-chloro-3-[4-(4-chlorobenzyloxy)phenyl]-propionate, melting point: 161°–162° C.

EXAMPLE 6-(1)

In 40 ml. of acetone is dissolved 5.3 g. of 4-(3-phenoxypropyl)aniline hydrochloride, followed by the addition of 5 ml. of hydrochloric acid, and the mixture is kept at not higher than 10° C. Under stirring, a solution of 1.52 g. of sodium nitrite in 3 ml. water is added and the mixture is kept at the same temperature for 30 minutes. To the mixture, 16 ml. of acrylic acid is added, and under stirring at 0°–5° C, cuprous oxide is added in small portions until evolution of gas has ceased. The reaction mixture is concentrated to dryness under reduced pressure. To the residue is added diluted hydrochloric acid and the mixture is subjected to extraction with benzene. The benzene layer is washed with water and an aqueous solution of 2 g. anhydrous sodium carbonate in 100 ml. water is added. The resultant crystals are heated to dissolve and then cooled. The crystals formed are collected by filtration and washed with a small volume of water and ethanol and dried under reduced pressure. The described procedure gives 4 g. of sodium 2-chloro-3-[4-(3-phenoxypropyl)phenyl] propionate. Melting point: 195°–196° C.

EXAMPLE 7-(1)

In 600 ml. of acetone is dissolved 70 g. of 4-(3-chlorobenzyloxy)aniline, followed by the addition of 100 ml. of hydrochloric acid. Under stirring and cooling with ice, a solution of 22.8 g. sodium nitrite in a sufficient volume of water to make 45 ml. is slowly added. The mixture is stirred under the same conditions for 30 minutes, after which 250 ml. of ethyl acrylate is added. While this reaction mixture is maintained at 24°–26° C, cuprous oxide is added in small portions until the evolution of gas has ceased. Then, 200 ml. of ether is added and the organic layer is washed three times with water. The solvent is thoroughly distilled off and the residue is dissolved in 900 ml. of ethanol. Under cooling with ice and stirring, a solution of 15 g. sodium hydroxide in a sufficient water to make 40 ml. is slowly added. Thereafter, the mixture is stirred under the same conditions for 1.5 hours and the resulting crystals are collected by filtration. Recrystallization from dilute ethanol yields 55 g. of sodium 2-chloro-3-[4-(3-chlorobenzyloxy)phenyl]-propionate, melting point: 205°–208° C.

EXAMPLE 8-(1)

In 10 ml. of water is dissolved 300 mg. of sodium 2-chloro-3-[4-(1-phenylpropyloxy)phenyl]propionate, followed by the addition of excess volume of aqueous solution of calcium chloride. The oily substance separated out is extracted with a mixture of ether and ethyl acetate (1:1). The extract is washed with water and the precipitate formed is filtered off. The solvent is distilled off and the residue is subjected to recrystallization from 4 ml. of 50% aqueous ethanol. The described procedure gives 150 mg. of calcium 2-chloro-3-[4-(1-phenylpropyloxy)phenyl]propionate. Melting point: 145° C

EXAMPLE 9-(1)

In 20 ml. of tetrahydrofuran is dissolved 1.0 g. of 2-chloro-3-[4-(1-phenylethyloxy)phenyl]propionic acid. Under cooling and stirring, 0.33 g. of triethylamine and then 0.34 g. of ethyl chlorocarbonate are added dropwise. The resultant white precipitates are filtered off. To the filtrate, 0.31 g. of aniline is added dropwise under cooling with ice and stirring. The mixture is stirred for about 2 hours. After tetrahydrofuran is distilled off, chloroform is added. The chloroform layer is washed with diluted hydrochloric acid and dried over magnesium sulfate. After the chloroform is distilled off, the resultant oil is purified by column chromatography, to give 580 mg. of oil. To this oil is added a mixture of petroleum ether and methanol, and the resultant crystals are collected by filtration. Recrystallization from petroleum ether gives N-phenyl-2-chloro-3-[4-(1-phenylethyloxy)phenyl]propionamide. Melting point: 90°–91° C.

EXAMPLES 9-(2) – 9-(3)

By a similar manner to Example 9-(1), the following compounds are produced.

| Example | Produced compound |
|---------|-------------------|
| 9-(2) | N-butyl-2-chloro-3-[4-(1-phenylethyloxy-phenyl]propionamide<br>oily substance<br>NMR spectrum (δppm, CDCl₃)<br>0.78(3H,t), 1.0–1.6(4H,m, 1.62(3H,d),<br>2.9–3.5(4H,m), 4.45(1H,t), 5.25(1H,q),<br>6.40(1H,br), 6.6–7.5(9H,m) |
| 9-(3) | N-methyl-N-butyl-2-chloro-3-[4-(1-phenyl-ethyloxy)phenyl]propionamide<br>oily substance<br>NMR spectrum (δppm, CDCl₃)<br>0.87(3H,t), 1.0–1.5(4H,m), 1.57(3H,d),<br>2.83(3H,s), 2.8–3.5(4H,m), 4.53(1H,t),<br>5.27(1H,q), 6.5–7.5(9H,m) |

COMPARATIVE EXAMPLES

To establish the superiority of the chloro compounds of this invention of the corresponding bromo compounds the following experiment was performed.

Experiment

1. Test Compound:

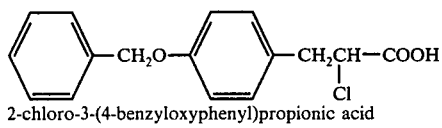

2-chloro-3-(4-benzyloxyphenyl)propionic acid (I)

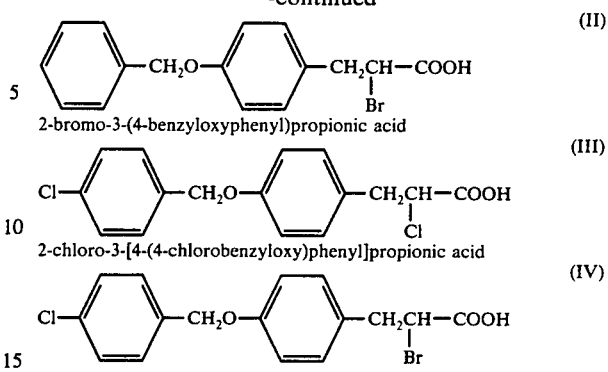

2. Animal employed in the test;
Male SD rats aged 8 to 9 weeks
3. Test method;
Blood lipid lowering effect:
One each of the test compounds was mixed in a laboratory chow purchased from CLEA Japan, Tokyo at a level cited in the table and fed to rats (5 rats for each group) for 4 days. Blood was taken from tail vein in the morning of the fifth day and used for the determination of plasma triglycerides (TG) and total cholesterol (TC).
4. Result;
The result is shown in the following Table.

| Compounds | Dose (% in diet) | Plasma (mg/100 ml) TG | TC |
|-----------|------------------|------|------|
| Control | 0 | 192±36 ⎫* | 71±9 ⎫* |
| (I) | 0.02 | 120±8 | 50±9 |
| (II) | 0.02 | 191±52 ⎭ | 69±8 ⎭ |
| Control | 0 | 197±32 ⎫* | 74±7 ⎫* |
| (III) | 0.01 | 69±19 | 53±6 |
| (IV) | 0.01 | 157±36 ⎭ | 75±8 ⎭ |

(note)
Significance of difference was ascertained with Student's t-test.
*: P<0.02

Conclusion

It is concluded that compound (I) is superior to compound (II) in hypolipidemic activity.
It is also concluded that compound (III) is superior to compound (IV) in hypolipidemic activity.
We claim:
1. A compound of the formula:

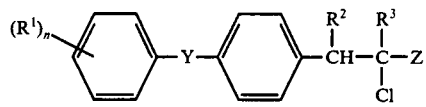

wherein $R^1$ represents hydrogen, lower alkyl having 1 to 5 carbon atoms, halogen, hydroxyl, lower alkoxy having 1 to 4 carbon atoms or trifluoromethyl; $R^2$ and $R^3$ are the same or different and each represents hydrogen or lower alkyl having 1 to 5 carbon atoms; Y represents alkylenoxy having 1 to 6 carbon atoms or alkylenedioxy having 1 to 6 carbon atoms; Z represents a carboxyl group or group convertible to a carboxyl group which is an aminocarbonyl group, an alkoxycarbonyl group having 2 to 5 carbon atoms, a mono- or di-alkylaminocarbonyl group having 2 to 9 carbon atoms or mono- or di-arylaminocarbonyl group having 7 to 16 carbon atoms and $n = 1$ or 2.

2. A compound as claimed in claim 1, wherein Y is an alkyleneoxy group having 1 to 6 carbon atoms.

3. A compound as claimed in claim 1, wherein Y is an alkylenedioxy group having 1 to 6 carbon atoms.

4. A compound as claimed in claim 1, wherein $R^2$ is hydrogen atom.

5. A compound as claimed in claim 1, wherein $R^2$ is an alkyl group having 1 to 5 carbon atoms.

6. A compound as claimed in claim 1, wherein $R^3$ is hydrogen atom.

7. A compound as claimed in claim 1, wherein $R^3$ is an alkyl group having 1 to 5 carbon atoms.

8. A compound as claimed in claim 1, wherein $R^1$ is hydrogen atom.

9. A compound as claimed in claim 1, wherein $R^1$ is a lower alkyl group having 1 to 5 carbon atoms.

10. A compound as claimed in claim 1, wherein $R^1$ is a halogen atom.

11. A compound as claimed in claim 1, wherein $R^1$ is an alkoxy group having 1 to 4 carbon atoms.

12. A compound as claimed in claim 1, wherein Z is carboxyl group.

13. A compound as claimed in claim 1, wherein the compound is 2-chloro-3-(4-benzyloxyphenyl)propionic acid.

14. A compound as claimed in claim 1, wherein the compound is 2-chloro-3-(4-benzyloxyphenyl)propionamide.

15. A compound as claimed in claim 1, wherein the compound is ethyl 2-chloro-3-(4-benzyloxyphenyl)propionate.

16. A compound as claimed in claim 1, wherein the compound is 2-chloro-3-[4-(4-chlorobenzyloxy)-phenyl]propionic acid.

17. A compound as claimed in claim 1, wherein the compound is ethyl 2-chloro-3-[4-(4-chlorobenzyloxy)-phenyl]propionate.

18. A compound as claimed in claim 1, wherein the compound is 2-chloro-3-[4-(3-chlorobenzyloxy)-phenyl]propionic acid.

19. A compound as claimed in claim 1, wherein the compound is ethyl 2-chloro-3-[4-(2chlorobenzyloxy)-phenyl]propionate.

20. A compound as claimed in claim 1, wherein the compound is ethyl 2-chloro-3-[4-(4-fluorobenzyloxy)-phenyl]propionate.

21. A compound as claimed in claim 1, wherein the compound is 2-chloro-3-[4-(1-phenylethyloxy)phenyl]-propionic acid.

22. A compound as claimed in claim 1, wherein the compound is ethyl 2-chloro-3-[4-(1-phenylethyloxy)-phenyl]propionate.

23. A compound as claimed in claim 1, wherein the compound is 2-chloro-3-[4-(1-phenylpropyloxy)-phenyl]propionic acid.

24. A compound as claimed in claim 1, wherein the compound is ethyl 2-chloro-3-[4-(1-phenylpropyloxy)-phenyl]propionate.

25. A compound as claimed in claim 1, wherein the compound is ethyl 2-chloro-3-[4-(1-methyl-2-phenylethyloxy) phenyl]-propionate.

26. A compound as claimed in claim 1, wherein the compound is ethyl 2-chloro-3-(4-phenoxymethylphenyl)propionate.

27. A compound as claimed in claim 1, wherein the compound is ethyl 2-chloro-3-[4-(1-phenoxyethyl)-phenyl]propionate.

28. A compound as claimed in claim 1, wherein Z is a pharmaceutically acceptable salt of carboxyl.

29. A compound as claimed in claim 1, which is sodium 2-chloro-3-[4-(1-phenylethyloxy)phenyl]propionate.

30. A compound as claimed in claim 1, which is sodium 2-chloro-3-[4-(1-phenylethyloxy)phenyl]propionatemonohydrate.

* * * * *